US005490085A

United States Patent [19]

Lambert et al.

[11] Patent Number: 5,490,085
[45] Date of Patent: Feb. 6, 1996

[54] METHOD FOR OPTIMIZING CONTROL OF A PRODUCTION UNIT

[75] Inventors: Didier C. Lambert, Lavera; Andre Martens, Chateauneuf les Martigues, both of France

[73] Assignees: BP Oil International Limited; BP Chemicals Limited, both of London, United Kingdom

[21] Appl. No.: 483,568

[22] Filed: Jun. 6, 1995

Related U.S. Application Data

[63] Continuation of Ser. No. 387,396, Feb. 13, 1995, abandoned, which is a continuation of Ser. No. 261,748, Jun. 17, 1994, abandoned, which is a continuation of Ser. No. 146,628, Oct. 29, 1993, abandoned, which is a continuation of Ser. No. 808,040, Dec. 12, 1991, abandoned, which is a continuation of Ser. No. 159,799, Feb. 24, 1988, abandoned.

[30] Foreign Application Priority Data

Feb. 27, 1987 [FR] France .................................. 87 02686

[51] Int. Cl.$^6$ .............................. G01J 3/42; G01N 33/22
[52] U.S. Cl. ...................... 364/500; 364/499; 250/339.07
[58] Field of Search ..................................... 364/496, 497, 364/498, 499, 500, 502; 356/303, 319, 326, 346, 436, 437; 250/226, 339.07, 339.08, 339.09, 339.12

[56] References Cited

U.S. PATENT DOCUMENTS

| | | | |
|---|---|---|---|
| 3,121,677 | 2/1964 | Coggeshall et al. | 208/178 |
| 3,666,932 | 5/1972 | White | 235/151.12 |
| 3,693,071 | 9/1972 | Dolbeau | 324/0.5 R |
| 3,896,312 | 7/1975 | Brown et al. | 250/343 |
| 4,236,076 | 11/1980 | Judge et al. | 250/347 |
| 4,251,870 | 2/1981 | Jaffe | 364/500 |
| 4,286,327 | 8/1981 | Rosenthal et al. | 364/497 |
| 4,323,777 | 4/1982 | Baskins et al. | 250/339 |
| 4,433,239 | 2/1984 | Thompson | 250/339 |
| 4,591,718 | 5/1986 | Amer | 250/339 |
| 4,642,778 | 2/1987 | Hieftje et al. | 364/497 |
| 4,692,883 | 9/1987 | Nelson et al. | 364/497 |
| 4,701,838 | 10/1987 | Swinkels et al. | 364/164 |
| 4,800,279 | 1/1989 | Hieftje et al. | 250/339 |
| 4,839,516 | 6/1989 | Freeman et al. | 250/255 |
| 5,303,165 | 4/1994 | Ganz et al. | 354/571.01 |
| 5,397,899 | 3/1995 | DiFoggio et al. | 250/339.09 |
| 5,412,581 | 5/1995 | Tackett | 364/498 |
| 5,430,295 | 7/1995 | leFebre et al. | 250/340 |

FOREIGN PATENT DOCUMENTS 8404594  11/1984  WIPO .

OTHER PUBLICATIONS

Preprint Publication entitled, "Prediction of Gasoline Octane Numbers by Near Infrared Spectroscopy in the Spectral Range 660–1215 nm," J. J. Kelly, C. H. Barlow, T. M. Jingujia, & J. B. Callis) CPAC Washington, Seattle. (1989).
Fredricks et al. "Rapid Coal Characterisation by FT–IR Spectroscopy", Jan. 1984, pp. 139–141, *Fuel.*
Fredricks et al. "Materials Characterization Using Factor Analysis of FT–IR Spectra. Part 1; Results", *Applied Spectroscopy,* vol. 39 No. 2 pp. 303–310 (1985).
Fredricks et al. "Materials Characterisation Using Factor Analysis of FT–Ir Spectra. Part 2: Mathematical and Statistical Considerations", *Applied Spectroscopy,* vol. 39 No. 2 pp. 311–316, (1985).
Fraim et al. "Natural Gas Heating Valve Determination using an Infrared Calorimeter", undated.
Jones et al., Chemical Engineering, Oct. 9, 1978, pp. 111–114, "Near Infrared Analyzers Refine process Control".
Jones Instrument Society Bulletin No. 0-87644-687-9, (1982), pp. 21–25 "Near–Infrared Analysis In The process Industry".
Murrill, Instrument Society of America, (1981), pp. 12 . 15 "Fundamental of Process Control Theory".
Callis et al., Analytical Chemistry, (59), No. 9, May 1, 1987, "Process Analytical Chemistry" pp. 624A–626A, 628A, 630A, 632A, 635A, 637A.
Callis, Abstract submitted for Lecture, Aug. 8, 1986.
Illman et al., Abstract submitted for Workshop, Sep. 1, 1986.
Callis, Lecture Notice, Sep. 22, 1986.
Callis, Abstract submitted for lecture, Sep. 24, 1986.
Callis, Abstract for Lecture, Nov. 5–7, 1986.
Callis, Abstrct for Paper in Analytical Chemistry, undated.
Avery et al, "Infra–red Spectra of Hydrocarbons. II Analysis of Octane Mixtures by the Use of Infra–red Spectra obtained at Low Temperatures", J. Applied Physics, vol. 18, Nov. 1947, pp. 960–967.
Healy et al, "A New Approach to Blending Octanes", API Division of Refining, 24th mid–year meeting (New York City, Division of Refining 27 May 1959, vol. 39 III, 1959, 132–192).
Article: "New Method may Determine Octane Ratings of Gasoline Quicker, Better", Hydrocarbon Processing, Jul. 1987, p. 19.
Hibbard et al, "Carbon–Hydrogen Groups in Hydrocarbons", Analytical Chemistry, vol. 21, No. 4, pp. 486–492 (Apr. 1949).
Stark et al, "Near–Infrared Analysis (NIRA): A Technology for Quantitative and Qualitative Analysis", Applied Spectroscopy Reviews, 22(4), pp. 335–339 (1986).
Weyer, "Near–Infrared Spectroscopy of Organic Substances" Applied Spectroscopy Reviews, 21(1&2), 1–43 (1985).
Honigs, D. E., "Near–Infrared Analysis", Analytical Instrumentation, 14(1), 1–62 (1985).
Schoen et al, "Calculating Gasoline Blend Octane Ratings", Industrial and Engineering Chemistry, vol. 49, No. 9, pp. 1740–1742, Sep. (1985).

(List continued on next page.)

*Primary Examiner*—Michael Zanelli
*Attorney, Agent, or Firm*—Brooks Haidt Haffner & Delahunty

[57] ABSTRACT

The octane number of a product is directly determined from its near infrared (NIR) absorption spectrum in the wave number spectral range of from 6667 to 3840 centimeter $^{-1}$. A number (n) of frequencies is selected within this range, and the (n) absorbance values are correlated with the octane number by using a multivariate regression analysis.

10 Claims, No Drawings

OTHER PUBLICATIONS

Gary et al, Petroleum REfining, 2nd edition, Marcel Dekker, New York, 1984.

Myers et al, "Determination of Gasoline Octane Numbers from Chemical Composition" Analytical Chemistry, vol. 47, No. 13, pp. 2301–2304, Nov. 1975.

Honigs et al, "Near–Infrared Determination of Several Physical Properties of Hydrocarbons", Analytical Chemistry, vol. 57, No. 2, Feb. 1985, pp. 443–445.

Whetsel, K. B. "Near Infrared Spectrophotometry". Applied Spectroscopy Reviews, 2(1), 1–67) (1968).

Honigs et al, "Near–Infrared Reflectance Analysis by Gauss–Jordan Linear Algebra", Applied Spectroscopy, vol. 37, No. 6, 1983, pp. 491–497.

Borisevich et al, "Instrumentation and Automation Equipment Method for Determining Group Hydrocarbon Composition and the Octane Number of REforming Gasolines with IR Spectroscopy for Purposes of Operation Control", Automatizatsiyz; 1981, No. 3 pp. 13–15.

Dornheim et al, "Optimum Non–Linear Gasoline Blending", The Oil and Gas Journal, May 26, 1958.

InTech: The International Journal of Instrumentation and Control; *Instruments and Materials: The Synergism is Just Beginning;* Kenneth Ball; Mar. 1987; pp. 9–15.

*Mesures*, vol. 33 No. 6/7, Jun./Jul. 1968, pp. 96–99, Paris, FR: G. Goma et al: "Etude de la mesure en ligne de l'indice d'Octane, en particulier par chromatographic".

*Analytical Chemistry,* vol. 56 No. 8, Jul. 1984, pp. 933A–934 A, Easton, Pennsylvania, U.S.: "Near–infrared reflectance spectrometry: Tip of the iceberg".

*TRAC: Trends in Analytical Chemistry,* vol. 5, No. 6, Jun./Jul. 1986, pp. 154–157 Elsevier Science Publishers B. V., Amsterdam, NL; B. Buchanan, et al.: "Trends in infra–red analysis".

Lebedev, V. P.; Miroshnichenko, E. A.; Matyushin, Y. N.; Larinov, B. P.; Romanov, V. S.; Bukolov, Y. E.; Denisov, G. M.; Balepin, A. A.; Lebedev, Y. A., *Zh. Fiz. Khim,* (1975), pp. 1928–1932.

American Society for Testing and Materials, "Standard Method of Test for Molecular Weight off Petroleum Oils from Viscosity Measurements", *Annual Book of ASTM Standards,* (1973), pp. 847–850.

Wetzel, David L., "Near–Infrared Reflectance Analysis", *Analytical Chemistry,* vol. 55, No. 12, (Oct. 1983), pp. 1165A–1166A, 1168A, 1170A, 1172A, 1174A, 1176A.

Watson, C. A., "Near Infrared Reflectance Spectrophotometric Analysis of Agricultural Products", Analytical Chemistry, vol. 49, No. 9 (Aug. 1977), pp. 835A–840A.

Starr, C.; Smith, D. B.; Blackman, J. A.; Gill, A. A., "Applications of Near Infrared Analysis in Breeding Wheats for Bread–Making Quality", *Anal. Proc.,* vol 20, (1983), pp. 72–74.

Winch, J. E. and Major, H., "Predicting Nitrogen and Digestability of Forages Using near Infrared Reflectance Photometry", *Can. J. Plant Sci.,* vol. 61, (Jan. 1981) pp. 45–51.

Norris, K. H.; Barnes, R. F.; Moore, J. E.; Shenk, J. S., "Predicting Forage Quality by Infrared Reflectance Spectroscopy", *Journal of Animal Science,* vol. 43, No. 4, (1976) pp. 889–897.

Rose, John J., "Analysis of Parenteral Drugs by NIRA", The Pittsburgh Conference, Atlantic City, N.J., (Mar. 1983), Paper 707.

Honigs, D. E.; Heiftje, G. M.; Hirschfeld, T., "A New Method for Obtaining Individual Component Spectra from Those of Complex Mixtures", *Applied Spectroscopy,* vol. 38, No. 3, (1984), pp. 317–322.

Honigs, D. E.; Freelin, J. M.; Hieftje, G. M.; Hirschfeld, T. B., "Near–Infrared Reflectance Analysis By Gauss–Jordan Linear Algebra", *Applied Spectroscopy,* vol. 37, No. 6, (1983), pp. 491–497.

Weast, R. C. and Astle, M. J., Eds., *CRC Handbook of Chemistry and Physics,* 60th ed., (1979), pp. D–82 to D–84 [Table of Values of Chemical Thermodynamic Properties of Hydrocarbons].

Goddu, Robert F. and Delker, Dorothy A., "Spectra–Structure Correlations for the Near–Infrared Region", *Analytical Chemistry,* vol. 32, No. 1, (Jan. 1960), pp. 140–141.

Kaye, Wilbur, "Near–Infrared Spectroscopy—I. Spectral Identification and Analytical Applictions", *Spectrochimica Acta,* vol. 6, (1954), pp. 257–287.

Whetsel, K. B., "Near–Infrared Spectrophotometry", *Applied Spectroscopy Reviews,* vol. 2(1), (1968), pp. 1–67.

Hirschfeld, T. and Stark, E., "Near–Infrared Reflectance Analysis of Foodsturfs", *Analysis of Foods and Beverages,* Chakrabarty, E., Ed., (1984), pp. 505–551.

METHOD FOR OPTIMIZING CONTROL OF A PRODUCTION UNIT

This application is a continuation of application Ser. No. 08/387,396 filed Feb. 13, 1995, which is a continuation of application Ser. No. 08/261,748 filed Jun. 17, 1994, which is a continuation of application Ser. No. 08/146,628 filed Oct. 29, 1993, which is a continuation of application Ser. No. 07/808,040 filed Dec. 12, 1991, which is a continuation of application Ser. No. 07/159,799 filed Feb. 24, 1988, all of said antecedent applications being now abandoned.

The invention relates to a method for the determination of the octane number of petroleum products using near infrared (NIR) spectroscopy.

There are several octane numbers, including the motor octane number and the research octane number, defined in particular by the French Standard NF M07-026 dated January 1986 using the methods ASTM D 2699 and D 2700, under international arrangements, in Standards TSO 5163 and 5164. The measurement method defined by these Standards is complex since it involves a special internal combustion engine, and requires meticulous control of various parameters for comparing the operation of the engine with the motor fuel under test and with a reference fuel. By definition, the method is precise since it is one that defines the values obtained, but it is not very repeatable, having a repeatability limit of 0.5 to 1.2 depending on the octane level determined. However, it is tedious and time-consuming to perform because of the equipment used and the number of operations that are necessary.

In research, and particularly in production operations, it would be desirable to determine octane numbers with sufficient precision, in a simpler, less tedious, and above all quicker and more repeatable manner with a repeatability varying from 0.1 to 0.2.

Correlations have been established between the chemical composition of a product in terms of its several components, and its octane number, the composition being determined by various means such as chromatography or nuclear magnetic resonance.

IR spectroscopic analysis is not generally used for determining the composition of petroleum products. If it is, the far infrared region is used, because the near infrared band is extremely complex for determining product compositions.

It is an object of the present invention to provide a simple, rapid and reliable method for the direct determination of the octane number without determining the chemical composition of the product undergoing examination.

According to the present invention there is provided a method for the direct determination of the octane number of a product from its near infrared (NIR) absorption spectrum in the wave number spectral range from 6667 to 3840 cm$^{-1}$, preferably 4800 to 4000 cm$^{-1}$ which method comprises selecting a number (n) of frequencies within this range and correlating the (n) absorbance values with octane number, the correlation being achieved by means of multivariate regression analysis.

The correlation depends on the type of spectrometer used, the type of octane number required, and the number (n) of the frequencies used.

(n) is suitably between 1 and 200 and preferably between 1 and 30.

A feature of the invention is the use of radiation in the near infrared, in the 1.5μ to 2.6μ band (6687 to 3840 cm$^{-1}$), preferably the 2.1μ to 2.5μ band (4800 to 4000 cm$^{-1}$), which, as explained above, is not normally used since it is made up of absorption bands that are combined in a complex manner; on the other hand, it ensures better repeatability for operating the method according to the invention.

Good results are obtained by using the following 15 frequencies expressed as the wave number (per centimeter), or frequencies of values close to these:

$F_1 = 4670$ cm$^{-1}$
$F_2 = 4640$
$F_3 = 4615$
$F_4 = 4585$ cm$^{-1}$
$F_5 = 4485$
$F_6 = 4385$
$F_7 = 4332$
$F_8 = 4305$
$F_9 = 4260$
$F_{10} = 4210$
$F_{11} = 4170$
$F_{12} = 4135$
$F_{13} = 4100$
$F_{14} = 4060$
$F_{15} = 4040$

In this case the baseline is taken at 4780 cm$^{-1}$. The corresponding frequency expressed in practical units (Hz) is obtained by multiplying these values by $3.10^{10}$—the velocity of light in cm/s.

An infrared spectrometer is used, e.g. Perkin Elmer model 1750, with a Fourier transform, provided with a 500 u sodium chloride cell in which a sample of the product is placed. Using the classic procedure, the absorbance, i.e. the logarithm of the ratio of the reduction between the incident radiation and the radiation after passing through the cell, is determined for each frequency.

The spectrometer used measures the absorbances $ABS_i$, for the 15 significant frequencies $F_i$ selected, the octane number ON being calculated directly by means of a linear expression with a constant term C and appropriate multiplication coefficients $A_i$:

$$ON = C + \Sigma ABS_i \times A_i$$

Table 1 hereafter gives the values of these terms C and $A_i$ respectively, for the six following types of octane number:

clear research octane number (RON CLR)

research octane number with 0.15 g/l lead tetraethyl (RON 0.15)

research octane number with 0.4 g/l lead tetraethyl (RON 0.4)

clear motor octane number (MON CLR)

motor octane number with 0.15 g/l of lead tetraethyl (MON 0.15)

motor octane number with 0.4 g/l lead tetraethyl (MON 0.4)

Other octane numbers can also be determined in the same way, for example, those of leaded gasolines with other lead alkyls, e.g. tetramethyl lead.

TABLE 1

|  | RON CLR | RON 0.15 | RON 0.4 | MON CLR | MON 0.15 | MON 0.4 |
| --- | --- | --- | --- | --- | --- | --- |
| C | 94.94 | 135.88 | 93.30 | 82.56 | 89.81 | 89.42 |
| $A_1$ | 271.30 | 0 | 39.84 | −204.35 | −121.17 | −231.42 |
| $A_2$ | −0.54 | 0 | −69.56 | 382.25 | 0 | 453.95 |
| $A_3$ | −209.08 | 0 | −105.05 | −73.26 | −107.81 | −147.28 |
| $A_4$ | −14.24 | 0 | 75.88 | −97.77 | 112.83 | −18.16 |
| $A_5$ | 16.51 | 46.52 | 20.93 | 2.39 | −36.83 | −107.71 |
| $A_6$ | 28.84 | 47.80 | 37.80 | 21.41 | 76.71 | 73.12 |
| $A_7$ | 26.05 | 0 | 30.14 | −0.12 | 0 | −13.56 |
| $A_8$ | 16.28 | −12.46 | 1.17 | 32.46 | −1.01 | 54.12 |
| $A_9$ | 16.03 | −44.96 | 11.85 | −43.20 | −2.92 | −66.38 |
| $A_{10}$ | −96.80 | −106.30 | −223.22 | −118.47 | −92.33 | −250.18 |
| $A_{11}$ | −25.69 | −11.59 | 41.77 | 0.65 | −49.24 | 81.21 |
| $A_{12}$ | 91.10 | 73.51 | 159.45 | 124.37 | 0 | 78.54 |
| $A_{13}$ | −141.96 | 0 | −179.25 | −71.57 | −28.35 | 20.64 |
| $A_{14}$ | −27.62 | −22.47 | 5.28 | 18.64 | 0 | −9.39 |
| $A_{15}$ | 56.30 | 0 | 74.70 | 21.50 | 76.57 | 33.64 |
| Motor/IR residual standard deviation | 0.212 | 0.151 | 0.193 | 0.252 | 0.291 | 0.273 |
| IR Repeatability | 0.21 | 0.12 | 0.15 | 0.17 | 0.13 | 0.22 |

If the spectrometer is equipped with means for calculation and a memory as in the type indicated, it is sufficient to program it and load the memory using the values given in the table. Otherwise, it can be connected to a computer which will carry out this operation.

By way of example, the results of the absorbance measurements obtained from 5 different gasolines are given in the upper part of the following Table 2. The values of the six corresponding octane numbers, as given by the method according to the present invention, are shown in the bottom part of the Table and compared with those in the mid part which were determined by the standard procedure.

By comparing the results obtained by this method with those obtained by the conventional ASTM method, it can be shown that the precision obtained is very satisfactory.

The same method could, of course, be employed using slightly different frequencies $F_i$ or a number of them (n) greater or less than 15 (between 1 and 200), or again, with a different spectrometer, determining each time the different terms C and $A_i$ by multi-variable regression.

If the product is intended to be "leaded", the method gives, beforehand, the octane number which will be obtained after the addition of lead alkyls. The method can be used for gasolines whether or not they contain lead alkyls, the latter

TABLE 2

|  | Gasoline 1 | Gasoline 2 | Gasoline 3 | Gasoline 4 | Gasoline 5 |
| --- | --- | --- | --- | --- | --- |
| $F_1 = 4670$ | 0.06008 | 0.15214 | 0.09552 | 0.06692 | 0.10917 |
| $F_2 = 4640$ | 0.06201 | 0.13162 | 0.09383 | 0.00681 | 0.10700 |
| $F_3 = 4615$ | 0.08608 | 0.15967 | 0.13218 | 0.09455 | 0.15164 |
| $F_4 = 4585$ | 0.06532 | 0.13226 | 0.09167 | 0.06753 | 0.10789 |
| $F_5 = 4485$ | 0.07865 | 0.07443 | 0.05108 | 0.08144 | 0.06739 |
| $F_6 = 4385$ | 0.52602 | 0.43641 | 0.49470 | 0.52258 | 0.49834 |
| $F_7 = 4332$ | 0.84231 | 0.60741 | 0.73268 | 0.80791 | 0.73177 |
| $F_8 = 4305$ | 0.68969 | 0.52745 | 0.62381 | 0.68184 | 0.64397 |
| $F_9 = 4260$ | 0.63882 | 0.51533 | 0.53247 | 0.62656 | 0.56382 |
| $F_{10} = 4210$ | 0.41042 | 0.32350 | 0.36748 | 0.39421 | 0.37351 |
| $F_{11} = 4170$ | 0.41526 | 0.32331 | 0.36939 | 0.39696 | 0.36120 |
| $F_{12} = 4135$ | 0.38551 | 0.30219 | 0.33786 | 0.37445 | 0.33837 |
| $F_{13} = 4100$ | 0.39272 | 0.34255 | 0.35733 | 0.38637 | 0.36765 |
| $F_{14} = 4060$ | 0.54368 | 0.77413 | 0.60849 | 0.55774 | 0.64733 |
| $F_{15} = 4040$ | 0.44967 | 0.54314 | 0.53872 | 0.46912 | 0.56592 |
| Measured |  |  |  |  |  |
| RON CLR | 91.7 | 95.8 | 93.2 | 93.0 | 92.0 |
| RON 0.15 | 95.0 | 97.9 | 97.5 | 96.5 | 95.8 |
| RON 0.4 | 96.0 | 99.3 | 99.1 | 98.1 | 97.9 |
| MON CLR | 78.2 | 82.2 | 83.9 | 79.6 | 81.8 |
| MON 0.15 | 81.0 | 84.2 | 87.7 | 82.3 | 85.9 |
| MON 0.4 | 82.5 | 85.2 | 92.3 | 84.1 | 88.6 |
| Calculated |  |  |  |  |  |
| RON CLR | 91.4 | 95.8 | 93.3 | 92.8 | 92.5 |
| RON 0.15 | 95.0 | 97.2 | 98.0 | 96.5 | 95.9 |
| RON 0.4 | 95.9 | 99.3 | 99.2 | 97.6 | 97.7 |
| MON CLR | 78.3 | 82.2 | 84.0 | 79.8 | 82.4 |
| MON 0.15 | 80.5 | 83.9 | 87.2 | 82.7 | 86.5 |
| MON 0.4 | 82.7 | 85.2 | 92.3 | 84.4 | 88.1 | being used in amounts which are too low to affect the value of the absorbances. Thus, the correlation takes into account the susceptability of the gasoline to lead and the sensitivity, the sensitivity being defined for a given gasoline as the difference between RON and MON as determined by the previously described tests. This is valid whatever the amount of added lead. The method thus enables the clear research, clear motor, and leaded fuel octane numbers to be determined simultaneously.

The method is applicable to all types of internal combustion engine fuels whatever their composition as regards saturated, unsaturated and aromatic hydrocarbons. Suitable basestocks include straight run gasolines, steam-cracked gasolines, thermally-cracked or catalytically cracked gasolines, reformates, alkylates, hydrogenated gasolines and gasolines resulting from polymerisation, isomerisation, cyclisation, and dehydrogenation reactions, and other synthetic gasolines such as synfuels.

Where the product analysed contains oxygenated compounds used as anti-knock compounds, such as alcohols (e.g. t-butyl alcohol, methanol), aldehydes, ketones or ethers (e.g. methyl t-butyl ether), the method takes into account the fact that these compounds have been considered in establishing the statistical correlations.

Thus, the method according to the invention enables the determination, by means of a spectrometer, optionally equipped with a fibre optics system and optionally linked to a computer, of the octane number(s) which are of interest, virtually in real-time, and continuously.

In production, one application is the optimisation of the control of a production unit by measuring the octane number of the product and adjusting the feedback control of the unit in order to obtain a product with the desired octane number. This application requires the use of a process computer which may or may not be involved in the control system, for example, at the outlets of the processing units producing the gasoline basestocks (reformers, thermal, catalytic and steam crackers, etc.).

Another application lies in automatically rendering the mixing process non-interactive by determining the octane number of each storage tank in order to determine, by calculation, the proportions of the products issued from the various tanks for transferring to the mixing tank and/or determining the octane number of the product obtained.

We claim:

1. In a process for optimizing the control of a production unit for making an internal combustion engine fuel product or base stock with a desired octane number, the improvement which comprises: (a) determining the octane number of said fuel product or base stock by (i) measuring the near infrared absorption of said fuel product or base stock within the wave number spectral range 4800–4000 $cm^{-1}$, and (ii) directly correlating by means of multivariate regression analysis the (n) absorbance values obtained with the octane number of said product or base stock; and (b) employing said determined octane number to control and optimize the process to produce said desired octane number.

2. The process according to claim 1 wherein (n) is in the range 1–200.

3. The process according to claim 2 wherein (n) is in the range 1–30.

4. The process according to claim 3 wherein the (n) frequencies used are selected from those defined by the following:

$F_1$=4670 $cm^{-1}$ $F_2$=4640 $cm^{-1}$ $F_3$=4615 $cm^{-1}$ $F_4$=4585 $cm^{-1}$ $F_5$=4485 $cm^{-1}$ $F_6$=4385 $cm^{-1}$ $F_7$=4332 $cm^{-1}$ $F_8$=4305 $cm^{-1}$ $F_9$=4260 $cm^{-1}$ $F_{10}$=4210 $cm^{-1}$ $F_{11}$=4170 $cm^{-1}$ $F_{13}$=4100 $cm^{-1}$ $F_{14}$=4060 $cm^{-1}$ $F_{15}$=4040 $cm^{-1}$

5. The process according to claim 1 wherein the correlations are not affected by a susceptibility of the product to lead alkyls.

6. The process according to claim 1 wherein the product is a gasoline.

7. The process according to claim 7 wherein the gasoline contains lead alkyls.

8. The process according to claim 6 whereof the gasoline contains oxygenated compounds.

9. The process according to claim 1 wherein at least one of the following octane numbers are determined simultaneously: clear research, clear motor, leaded research and leaded motor.

10. A process as claimed in claim 1, wherein the production unit is selected from the group consisting of reforming, thermal, and catalytic cracking units.

* * * * *

UNITED STATES PATENT AND TRADEMARK OFFICE
CERTIFICATE OF CORRECTION

PATENT NO.   : 5,490,085
DATED        : February 6, 1996
INVENTOR(S)  : DIDIER C. LAMBERT and ANDRE MARTENS It is certified that error appears in the above-indentified patent and that said Letters Patent is hereby corrected as shown below:

Column 6,
Claim 7, line 1, after "claim" change "7" to --6--.

Signed and Sealed this

Sixteenth Day of July, 1996

*Attest:*

BRUCE LEHMAN

*Attesting Officer*    Commissioner of Patents and Trademarks